US009244528B2

(12) United States Patent
Cleveland et al.

(10) Patent No.: US 9,244,528 B2
(45) Date of Patent: Jan. 26, 2016

(54) GAZE BASED COMMUNICATIONS FOR LOCKED-IN HOSPITAL PATIENTS

(71) Applicant: LC Technologies, Inc., Fairfax, VA (US)

(72) Inventors: Nancy Cleveland, Annandale, VA (US); Dixon Cleveland, Annandale, VA (US)

(73) Assignee: LC Technologies, Inc., Fairfax, VA (US)

( * ) Notice: Subject to any disclaimer, the term of this patent is extended or adjusted under 35 U.S.C. 154(b) by 0 days.

(21) Appl. No.: 13/857,250

(22) Filed: Apr. 5, 2013

(65) Prior Publication Data
US 2013/0265231 A1    Oct. 10, 2013

Related U.S. Application Data

(60) Provisional application No. 61/620,699, filed on Apr. 5, 2012.

(51) Int. Cl.
*G06F 3/01* (2006.01)
*G06F 3/048* (2013.01)
*G06F 19/00* (2011.01)

(52) U.S. Cl.
CPC ............ *G06F 3/013* (2013.01); *G06F 19/3406* (2013.01)

(58) Field of Classification Search
CPC ..... G06F 3/012; G06F 3/013; G06F 19/3406; G06F 19/36–19/366
See application file for complete search history.

(56) References Cited

U.S. PATENT DOCUMENTS 6,003,991 A * 12/1999 Viirre ............................ 351/206
8,593,578 B1 * 11/2013 Geronimi ..................... 348/739
8,723,798 B2 * 5/2014 Vernacchia ................... 345/168
2003/0218672 A1 * 11/2003 Zhang et al. ................ 348/14.16
2008/0269636 A1 * 10/2008 Burrows et al. ............... 600/559
2008/0270266 A1 * 10/2008 Keane .............................. 705/27
2014/0375586 A1 * 12/2014 de Leon et al. ................ 345/173

OTHER PUBLICATIONS

Ely, "Confusion Assessment Method for the ICU (CAM-ICU) Flowsheet," 2002.*
Costello et al., "Communication vulnerable patients in the pediatric ICU: Enhancing care through augmentative and alternative communication," J. of Pediatric Rehabilitation Medicine: An Interdisciplinary Approach 3 (2010) 289-301.*
Lupu et al., "Eye Tracking Based Communication System for Patient with Major Neoro-locomotor Disabilities," 2011 15th International Conference on System Theory, Control, and Computing (ICSTCC), p. 318-322.*

* cited by examiner

*Primary Examiner* — Quan-Zhen Wang
*Assistant Examiner* — Xuemei Zheng
(74) *Attorney, Agent, or Firm* — John R. Kasha; Kelly L. Kasha; Kasha Law LLC

(57) ABSTRACT

Effective patient-centered care in a hospital relies heavily on the ability of patients to communicate their physical needs to care givers. If a patient is unable to speak, he has limited means of communicating at a time when he needs it the most. The embodiments presented here, generally referred to as EyeVoice, include unobtrusive eye-operated communication systems for locked-in hospital patients who cannot speak or gesture. EyeVoice provides an alternate means of communication, allowing hospital patients to communicate with their care givers using their eyes in place of their voices. Simply by looking at images and cells displayed on a computer screen placed in front of them, patients are able to: answer questions posed by caregivers; specify locations, types and degrees of pain and discomfort; request specific forms of assistance; ask or answer care related questions, and help direct his own care.

20 Claims, 16 Drawing Sheets

CAN YOU HEAR ME?
LOOK AT THE APPROPRIATE ANSWER.

YES　　　　　NO

600

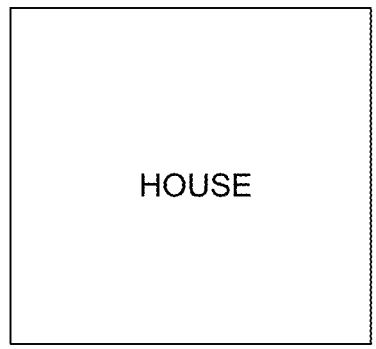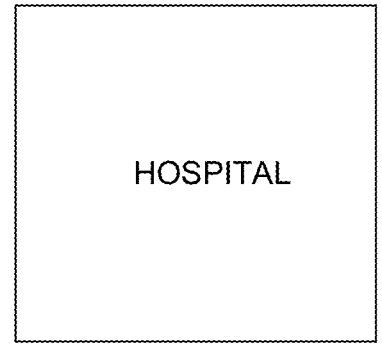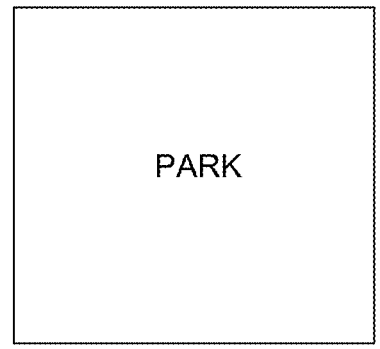
700
FIG. 7

CAM-ICU Worksheet

| Feature 1: Acute Onset or Fluctuating Course | Score | Check here if Present |
|---|---|---|
| Is the pt different than his/her baseline mental status? OR Has the patient had any fluctuation in mental status in the past 24 hours as evidenced by fluctuation on a sedation scale (i.e., RASS), GCS, or previous delirium assessment? | Either question Yes → | ☐ |
| Feature 2: Inattention | | |
| Letters Attention Test (See training manual for alternate Pictures) Directions: Say to the patient, "I am going to read you a series of 10 letters. Whenever you hear the letter 'A,' indicate by squeezing my hand." Read letters from the following letter list in a normal tone 3 seconds apart. S A V E A H A A R T Errors are counted when patient fails to squeeze on the letter "A" and when the patient squeezes on any letter other than "A." | Number of Errors >2 → | ☐ |
| Feature 3: Altered Level of Consciousness | | |
| Present if the Actual RASS score is anything other than alert and calm (zero) | RASS anything other than zero → | ☐ |
| Feature 4: Disorganized Thinking | | |
| Yes/No Questions (See training manual for alternate set of questions) 1. Will a stone float on water? 2. Are there fish in the sea? 3. Does one pound weigh more than two pounds? 4. Can you use a hammer to pound a nail? Errors are counted when the patient incorrectly answers a question. Command Say to patient: "Hold up this many fingers" (Hold 2 fingers in front of patient) "Now do the same thing with the other hand" (Do not repeat number of fingers) *If pt is unable to move both arms, for 2nd part of command ask patient to "Add one more finger" An error is counted if patient is unable to complete the entire command. | Combined number of errors >1 → | ☐ |
| Overall CAM-ICU Feature 1 plus 2 and either 3 or 4 present = CAM-ICU positive | Criteria Met → | ☐ CAM-ICU Positive (Delirium Present) |
| | Criteria Not Met → | ☐ CAM-ICU Negative (No Delirium) |

Copyright © 2002, E. Wesley Ely, MD, MPH and Vanderbilt University, all rights reserved Page 7

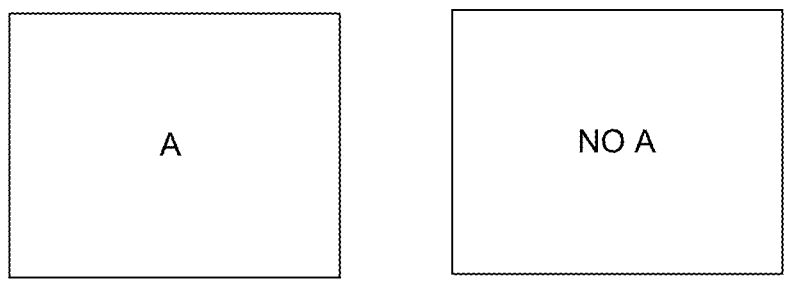
FIG. 9

GAZE BASED COMMUNICATIONS FOR LOCKED-IN HOSPITAL PATIENTS

CROSS-REFERENCE TO RELATED APPLICATION

This application claims the benefit of U.S. Provisional Patent Application No. 61/620,699, filed Apr. 5, 2012, which is incorporated by reference herein in its entirety.

INTRODUCTION

The ability to speak is often taken for granted, but for a significant number of hospital patients it can be a nearly impossible task. Patients who have been intubated, had brainstem strokes, spinal cord injury or traumatic brain injuries and those with ALS or SMA, may find themselves suddenly unable to communicate by verbal speech or manual sign. They are "locked-in"—unable to communicate their physical needs. Nurses must play a yes/no guessing game to get answers from these patients, but some crucial information, such as medical history and drug allergies, cannot be easily communicated by a yes or no signal.

Effective patient-centered care in a hospital relies heavily on the ability of patients to communicate their physical needs to care givers. If a patient is unable to speak, he has limited means of communicating at a time when he needs it most. Locked-in hospital patients need a better way to communicate with their nurses.

A number of studies have addressed communication problems with intubated patients. One study found that the majority of recently intubated patients experienced a high level of frustration when attempting to communicate their needs. In severe cases patients may be administered sedatives or placed in protective restraints when effective means of communication are not. Impairment in communication is a barrier to accurate assessment and optimum management of pain and delirium. Patients who can communicate and assist nurses in appropriate pain management recover more quickly and are able to be extubated earlier. The result is shorter hospital stays and reduced hospital expenses.

One group defined "patient-centered care" as care that makes the patient and their loved ones an integral part of the care team who collaborates with health care professionals in making clinical decisions. Patients who are unable to communicate cannot take part in decisions regarding their own care. These patients are denied access to patient-centered care because they do not have the tools they need to collaborate with their health care team.

SUMMARY

Effective patient-centered care in a hospital relies heavily on the ability of patients to communicate their physical needs to care givers. If a patient is unable to speak, due to injury or intubation for example, he has limited means of communicating at a time when he needs it most. Various embodiments of a system for communicating with locked-in patients are described below. An exemplary embodiment of such a system is, for example, EyeVoice system from LC Technologies Inc. In an embodiment, EyeVoice includes unobtrusive eye-operated communication systems for locked-in hospital patients who cannot speak or gesture. EyeVoice provides an alternate means of communication, allowing hospital patients to communicate with their caregivers using their eyes in place of their voices.

Simply by looking at images and cells displayed on a computer screen placed in front of them, patients are able to: answer questions posed by caregivers; specify locations, types and degrees of pain and discomfort; request specific forms of assistance; ask or answer care related questions, and help direct his own care. Nurses are able to administer delirium tests to patients who cannot normally physically respond to delirium oriented questions. A speech synthesizer in EyeVoice verbalizes the patient's visually selected communications, allowing the caregiver to hear the patient and allowing the patient to verify his communications.

Though likely most useful in hospital environments, Eye-Voice is intend for use throughout the medical system, both in-patient and out-patient, to facilitate patient communications in a broad set of medical situations. In addition to serving intubated patients, EyeVoice serves patients with a wide range of diseases and disabilities including ALS, MS, spinal cord injuries, traumatic brain injuries, muscular dystrophy, and brainstem strokes.

BRIEF DESCRIPTION OF THE DRAWINGS

FIG. 7 is an exemplary EyeVoice screen that displays cells with pictures of multiple possible answers for a patient to answer a particular question by looking at a particular cell, in accordance with various embodiments.

FIG. 8 is an exemplary delirium test referred to as the Confusion Assessment Method-ICU (CAM-ICU) test, in accordance with various embodiments.

FIG. 9 is an exemplary EyeVoice screen that presents a screen with two cells, labeled "A" and "No A," in which a patient simply looks at the "A" cell when he hears the letter A, in accordance with various embodiments.

Before one or more embodiments of the invention are described in detail, one skilled in the art will appreciate that the invention is not limited in its application to the details of construction, the arrangements of components, and the arrangement of steps set forth in the following detailed description or illustrated in the appendices. The invention is capable of other embodiments and of being practiced or being carried out in various ways. Also, it is to be understood that the phraseology and terminology used herein is for the purpose of description and should not be regarded as limiting.

DETAILED DESCRIPTION

Computer-Implemented System

Figure 2:
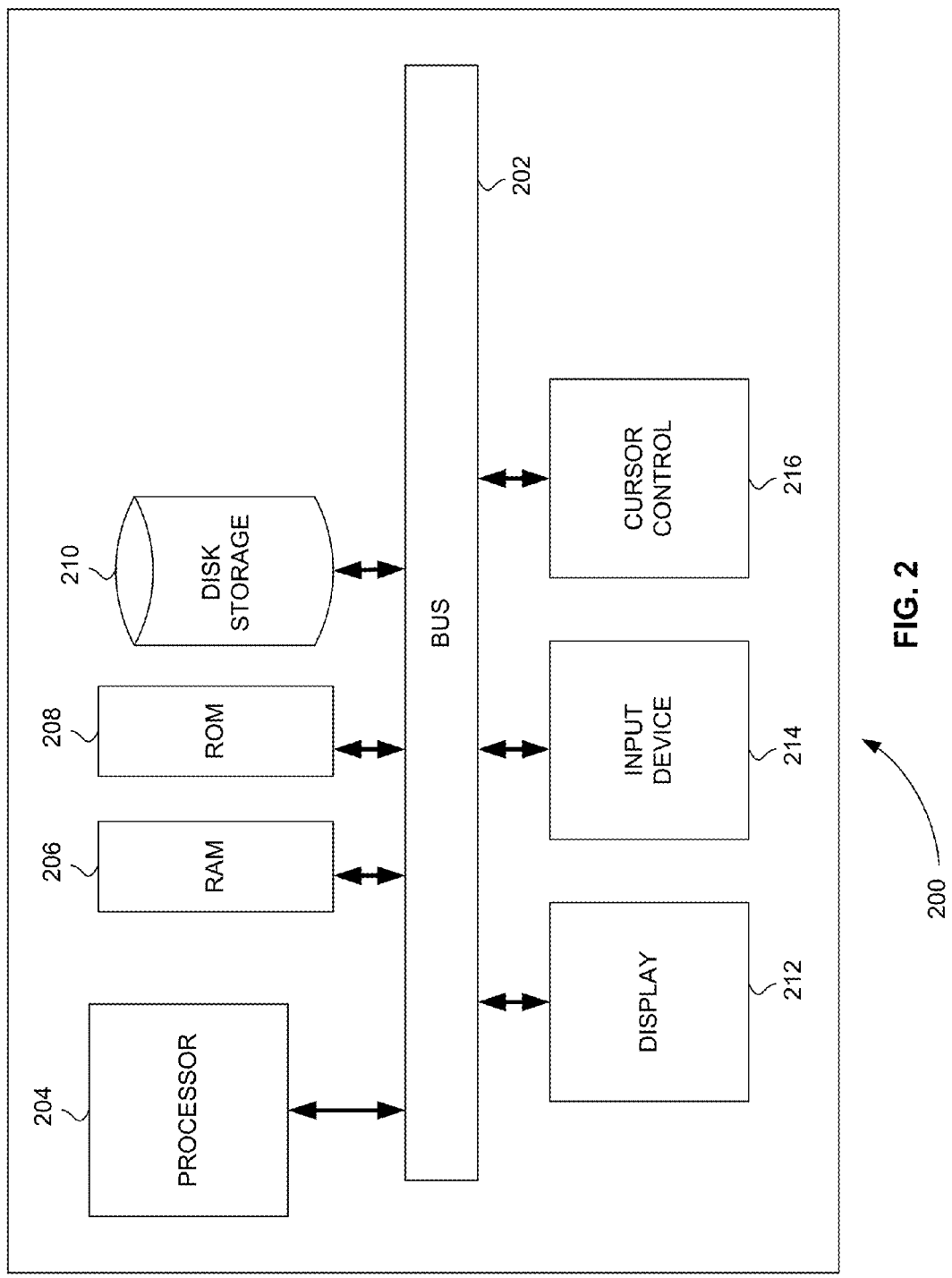
FIG. 2 is a block diagram that illustrates a computer system, in accordance with various embodiments.

FIG. 2 is a block diagram that illustrates a computer system 200, in accordance with various embodiments. Computer system 200 includes a bus 202 or other communication mechanism for communicating information, and a processor 204 coupled with bus 202 for processing information. Computer system 200 also includes a memory 206, which can be a random access memory (RAM) or other dynamic storage device, coupled to bus 202 for determining base calls, and instructions to be executed by processor 204. Memory 206 also may be used for storing temporary variables or other intermediate information during execution of instructions to be executed by processor 204. Computer system 200 further includes a read only memory (ROM) 208 or other static storage device coupled to bus 202 for storing static information and instructions for processor 204. A storage device 210, such as a magnetic disk or optical disk, is provided and coupled to bus 202 for storing information and instructions.

Computer system 200 may be coupled via bus 202 to a display 212, such as a cathode ray tube (CRT), liquid crystal display (LCD), or 3-dimensional display, for displaying information to a computer user. An input device 214, including alphanumeric and other keys, is coupled to bus 202 for communicating information and command selections to processor 204. Another type of user input device is cursor control 216, such as a mouse, a trackball or cursor direction keys for communicating direction information and command selections to processor 204 and for controlling cursor movement on display 212. This input device typically has two degrees of freedom in two axes, a first axis (i.e., x) and a second axis (i.e., y), that allows the device to specify positions in a plane.

A computer system 200 can perform the present teachings. Consistent with certain implementations of the present teachings, results are provided by computer system 200 in response to processor 204 executing one or more sequences of one or more instructions contained in memory 206. Such instructions may be read into memory 206 from another computer-readable medium, such as storage device 210. Execution of the sequences of instructions contained in memory 206 causes processor 204 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 204 for execution. Such a medium may take many forms, including but not limited to, non-volatile media, volatile media, and transmission media. Non-volatile media includes, for example, optical or magnetic disks, such as storage device 210. Volatile media includes dynamic memory, such as memory 206. Transmission media includes coaxial cables, copper wire, and fiber optics, including the wires that comprise bus 202.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 204 for execution. For example, the instructions may initially be carried on the magnetic disk of a remote computer. The remote computer can load the instructions into its dynamic memory and send the instructions over a telephone line using a modem. A modem local to computer system 200 can receive the data on the telephone line and use an infra-red transmitter to convert the data to an infra-red signal. An infra-red detector coupled to bus 202 can receive the data carried in the infra-red signal and place the data on bus 202. Bus 202 carries the data to memory 206, from which processor 204 retrieves and executes the instructions. The instructions received by memory 206 may optionally be stored on storage device 210 either before or after execution by processor 204.

In accordance with various embodiments, instructions configured to be executed by a processor to perform a method are stored on a non-transitory and tangible computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Eyetracker

In general, an eyetracker is a device that is used to determine where an eye is looking Modern eyetrackers, sometimes referred to as video eyetrackers, are camera-based devices that observe a person's eyes and predict the point in space where the person is looking. This point in space is referred to as the gazepoint, for example. The line connecting the fovea of the eye, the center of the eye pupil, and the gazepoint is referred to as the gaze line, for example.

Figure 1:
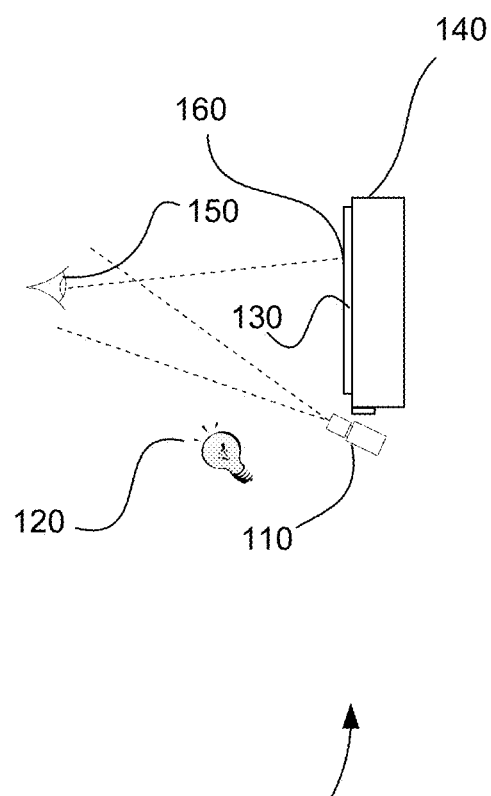
FIG. 1 is a schematic diagram of a system for communicating with locked-in patients, in accordance with various embodiments.

FIG. 1 is a schematic diagram showing an eyetracker 100, in accordance with various embodiments. Eyetracker 100 includes camera 110, illumination source 120, display screen 130 and processor 140. Illumination source 120 illuminates eye 150, and camera 110 images eye 150. Processor 140 receives the image from camera 110 and determines the gazepoint 160 of eye 150 on display 130. Eyetracker 100 can include additional elements. For example, eyetracker 100 can include one or more additional cameras (not shown) or one or more additional optical devices (not shown) to determine the range from camera 110 to eye 150.

Systems and Methods of Data Processing

The systems and methods for communicating with locked-in patients, such as EyeVoice, include an unobtrusive eye-operated communication system for locked-in hospital patients who cannot speak or gesture. The eye-operated communication system provides an alternate means of communication, allowing patients to communicate using their eyes in place of their voices and in some cases in place of their hands.

Figure 3:
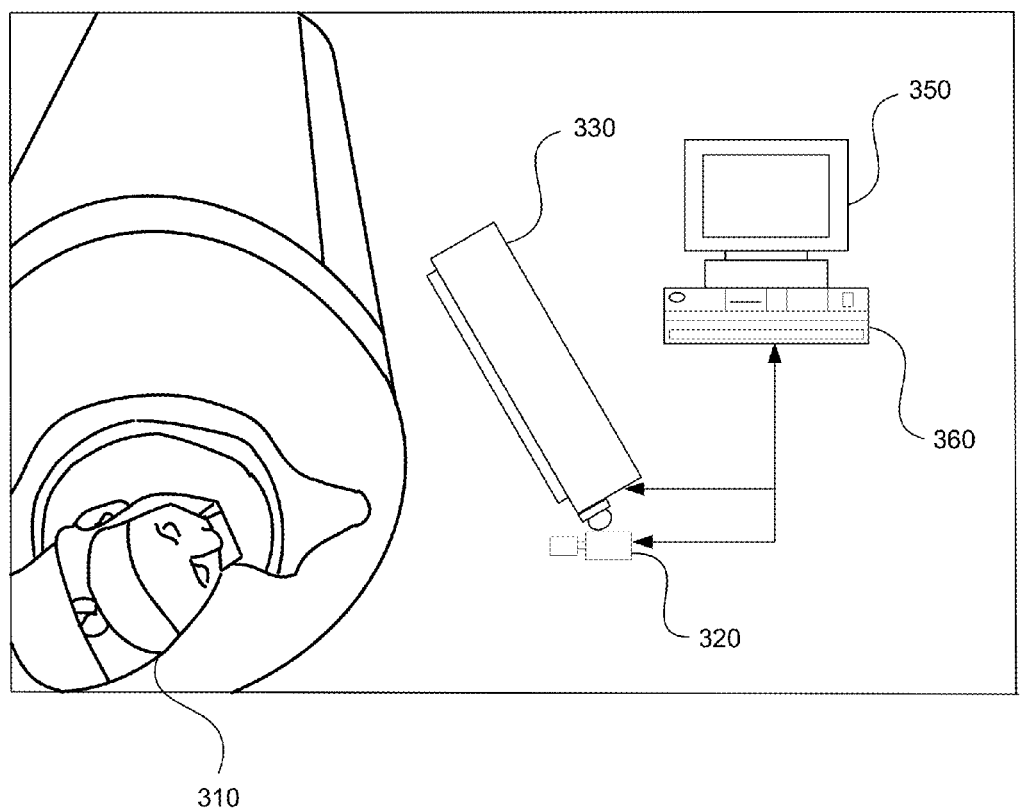
FIG. 3 is graphic showing a system for providing locked-in hospital patients a way to communicate effectively, in accordance with various embodiments.

FIG. 3 is graphic showing a system 300 for providing locked-in hospital patients a way to communicate effectively, in accordance with various embodiments. Patient 310 is a 16 year old with SMA. After admission to an ICU with pneumonia and being placed in an iron lung, patient 310 communicates with his nurses (not shown) using his eyes to run his Eyegaze Edge® from LC Technologies, Inc. For example, a nurse interacts with patient 310 by viewing a monitor 350 that is connected to a display 330 attached to an eyetracker 320 that monitors the patient's gazepoint (not shown) of the patient's eyes. Processor 360 analyzes the gazepoint trace of the patient's eyes to facilitate communication between patient 310 and the nurse.

Simply by looking at images and cells displayed on a computer screen placed in front of them, patients are able to: answer questions posed by caregivers; specify locations, types and degrees of pain and discomfort; request specific forms of assistance; and ask or answer care-related questions. Nurses are able to administer delirium tests such as the CAM-ICU test to patients who cannot normally physically respond to those questions. A speech synthesizer verbalizes the patient's visually selected communications, allowing the caregiver to hear the patient and allowing the patient to verify his communications.

Figure 4:
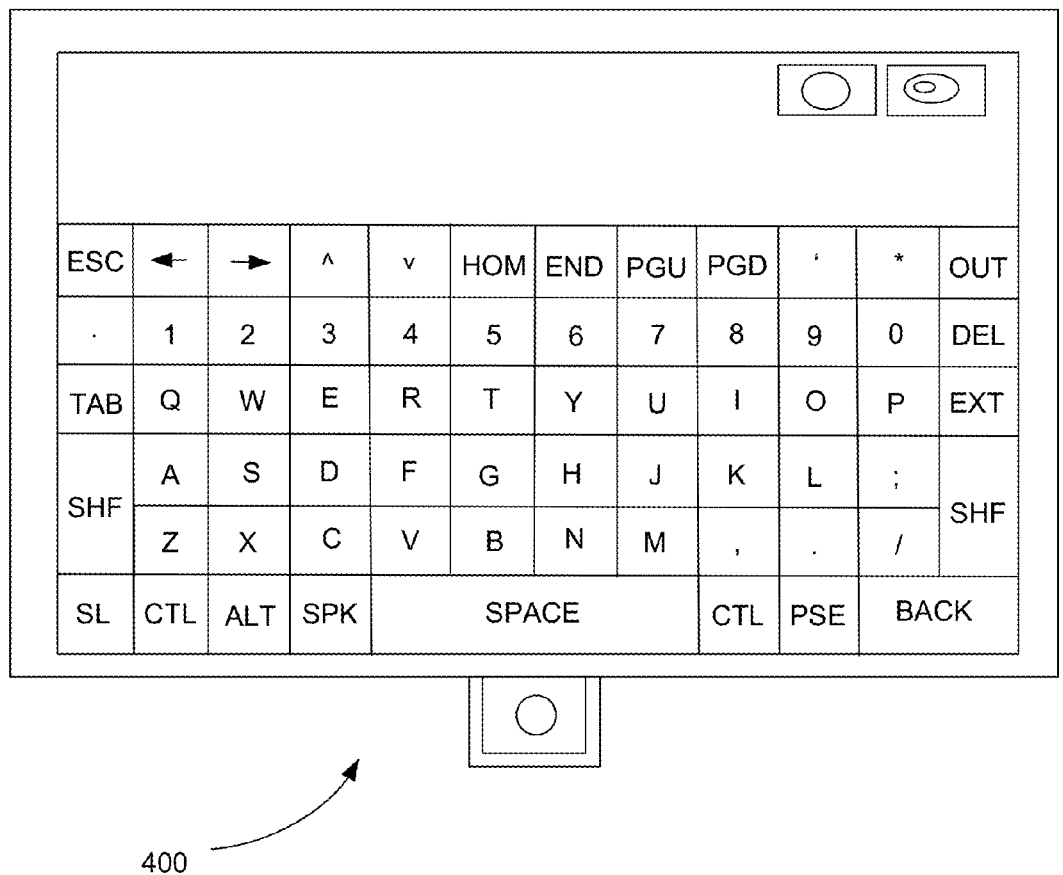
FIG. 4 shows an exemplary eyetracking device, in accordance with various embodiments.

The EyeVoice systems and methods for communicating with locked-in patients include eyetracking devices, i.e. devices that observe the patients' eyes and measure their gazepoint on a display such as a computer screen. FIG. 4 shows an exemplary eyetracking device 400: the LC Technologies Eyegaze Edge® which is currently used in home, school and work environments. A video camera mounted below a computer monitor observes the user's eyes as he looks around the screen, and sophisticated eye image processing software computes the coordinates of his gaze point. The user visually activates cells displayed on the screen by fixating his gaze on a cell for a specified period of time, typically a third to a half a second. A significant feature of the Eyegaze Edge includes a speech synthesizer that provides a voice to its user. The user may select, compose and verbalize text by visually activating displayed cells.

To meet hospital usage requirements for EyeVoice, the Eyegaze Edge® has several distinguishing features. To address equipment usability issues, a dual-screen configuration allows both the patient and nurse to see the displays easily, independently of how the patient is positioned for his comfort. The existing Eyegaze Edge® hardware is modified to be functional but not intrusive in the hospital; easy to maneuver into whatever position is necessary to accommodate the patient; removable in a matter of seconds in an emergency; easy to clean; and battery powered.

Figure 5:
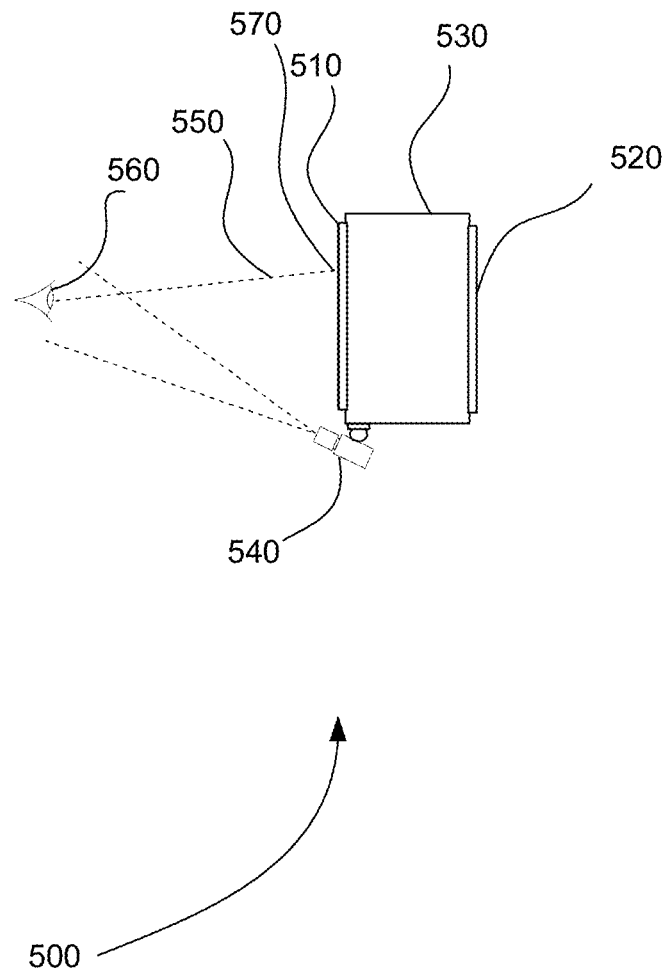
FIG. 5 is a schematic diagram of an EyeVoice system for communicating with locked-in patients, in accordance with various embodiments.

FIG. 5 is a schematic diagram of an EyeVoice system 500 for communicating with locked-in patients, in accordance with various embodiments. System 500 includes two video displays 510 and 520, processor 530, and video camera 540. Video display 510 displays information to a patient and display 520 displays information to a caregiver (not shown). Video camera 540 passively tracks the gaze line 550 of an eye 560 of a patient viewing video display 510. Processor 530 calculates an intersection of gaze line 550 of eye 560 with video display 510 and provides continuous feedback to processor 530 as to the gazepoint 570 where the patient is looking on display 510. Processor 530 correlates the patient's gazepoint trace with various information displayed on display 510.

In accordance with an embodiment of the present invention, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed. The terms "instructions configured to be executed" and "instructions to be executed" are meant to encompass any instructions that are ready to be executed in their present form (e.g., machine code) by a processor, or require further manipulation (e.g., compilation, decryption, or provided with an access code, etc.) to be ready to be executed by a processor.

At present nurses in a hospital ask their nonverbal patients to either hand write information or to point at pictures to communicate information. Those patients whose physical limitations make it impossible to use their hands are left with communications limited to yes/no responses. With EyeVoice, they make their needs known and answer nurses' questions clearly and quickly by simply looking at the appropriate image or words on a display screen.

Various embodiments of EyeVoice may include: 1) gaze-based patient orientation tests, 2) gaze-based versions of delirium tests, and 3) sets of patient-selected message screens, coupled with an on-screen keyboard, to enable patients to communicate their physical needs quickly and accurately with their eyes.

Gaze-Based Orientation and Awareness Assessment

When a nurse (caregiver) begins communicating with a patient, one of his early objectives is to establish the patient's current ability to communicate and to establish the patient's basic awareness of his particular situation. Once the caregiver knows the patient's communication ability and situational awareness, he adapts the level and content of his communications with the patient accordingly, to maximize the transfer of useful information to and from the patient.

If the current state of the patient's communication ability and awareness are not immediately obvious to the caregiver, he often performs different communication procedures to establish these abilities. Typical procedures include patient awareness and orientation tests. A key purpose of EyeVoice is to provide such awareness and orientation tests for patients who cannot speak.

Figure 6:
FIG. 6 is an exemplary EyeVoice screen that makes a hearing assessment by visually displaying the question, "Can you hear me?" in accordance with various embodiments.

At a very basic level in hospital communications, it is important to establish whether a patient can hear his caregiver. As illustrated in FIG. 6, an EyeVoice screen 600 can make this hearing assessment by visually displaying the question, "Can you hear me?" Because the "Can you hear me?" screen is typically one of the first Eyegaze screens a patient may see and visually interact with, the screen may also display explicit instructions to the patient to answer by looking at the appropriate cell. The patient answers the question by visually selecting one of 2 eye-activated cells, one labeled "yes" and the other "no."

In various embodiments, the EyeVoice system provides visual and or auditory feedback when the patient "visually" answers a question. For example, the selected cell or image may flash and/or a speech synthesizer may verbalize the patient's answer. The flash response provides useful feedback to the patient that he has triggered an action with his gaze alone, without having to use his hands or voice. The auditory response of the speech synthesizer indicates to the patient that the EyeVoice system is speaking for him, and it provides him confidence that he has a means to speak even if he cannot use his own voice.

If the patient is able to hear, the caregiver may continue his end of the conversation using his own voice, speaking normally. If the patient is unable to hear, alternative means of communications may be attempted. For example, if the patient is deaf but conscious and alert, it may be viable to display the caregiver communications in text displays that the patient may read from his Eyegaze screen.

Once a patient's hearing has been ascertained or an alternative means has been established for the caregiver to communicate to the patient (e.g., through written text), EyeVoice's gaze-based orientation tests may proceed to more direct questions to determine his situational awareness and level of consciousness.

At this stage in a hospital interview, a typical question is, "Do you know where you are?" In an EyeVoice implementation, the screen (shown as 700 in FIG. 7) may display cells with pictures of multiple possible answers, including, for example: a house, a hospital, a store, and a park. In this example, illustrated in FIG. 7, a patient oriented to place will answer the question by looking at the hospital cell. The next question may then be, "What year is it?" with several cells displaying different years. An additional question may be "What month is it?"

As illustrated in FIG. 5, in various embodiments, there are two display screens: one for the patient and the other for the caregiver. (As discussed earlier, the two screens allow both the patient and caregiver to see the displays comfortably, without limiting the patient position.) Typically, any screen that is displayed to the patient is also displayed to the caregiver. Additionally, however, the caregiver screen may include images of the patient's eyes and an indicator of where the patient is currently looking. This provides the caregiver with a) positive feedback that the eyetracking function is working, b) that the patient has his eyes opened or closed at any time, and c) an indication of what the patient is looking at as he looks around the screen and makes his visual selections. In addition to the patient's answers to the questions, the patterns of a patient's natural eye activity can often be a strong indicator of his cognitive ability to assess the screens he is viewing.

Until a patient has become accustomed to using EyeVoice communicate, nurses may verify a patient's gaze-based selections by asking the patient to make eye contact with the nurse if they meant yes or looking away for no.

Gaze-Based Delirium Test

In a hospital environment, delirium tests are used to obtain more detailed information about a patient's current level of consciousness and clearness of mind. A typical delirium test is the Confusion Assessment Method-ICU (CAM-ICU) test, illustrated in exemplary screen 800 of FIG. 8.

The EyeVoice's implementation for delirium tests allows nurses to administer a gaze-based version of delirium tests to locked-in patients who cannot speak or use their hands. For example, in Feature 2 of the CAM-ICU test: "Inattention—Letters Attention Test", the patient is asked to squeeze the nurse's hand whenever the patient hears the letter "a" in a sequence of letters that the nurse recites. As illustrated in FIG. 9, EyeVoice presents a gaze-based alternative to making the hand squeeze: a screen 900 with two cells, labeled "A" and "No A." The patient simply looks at the "A" cell when he hears the letter A.

Feature 4A of the CAM-ICU test: "Disorganized Thinking—Yes/No Questions Test" requires the patient to answer yes or no to a series of questions that require some level of cognitive thought. With EyeVoice, the patient may answer these questions with a "yes" and "no" screen (similar to that shown in FIG. 6).

Figure 10:
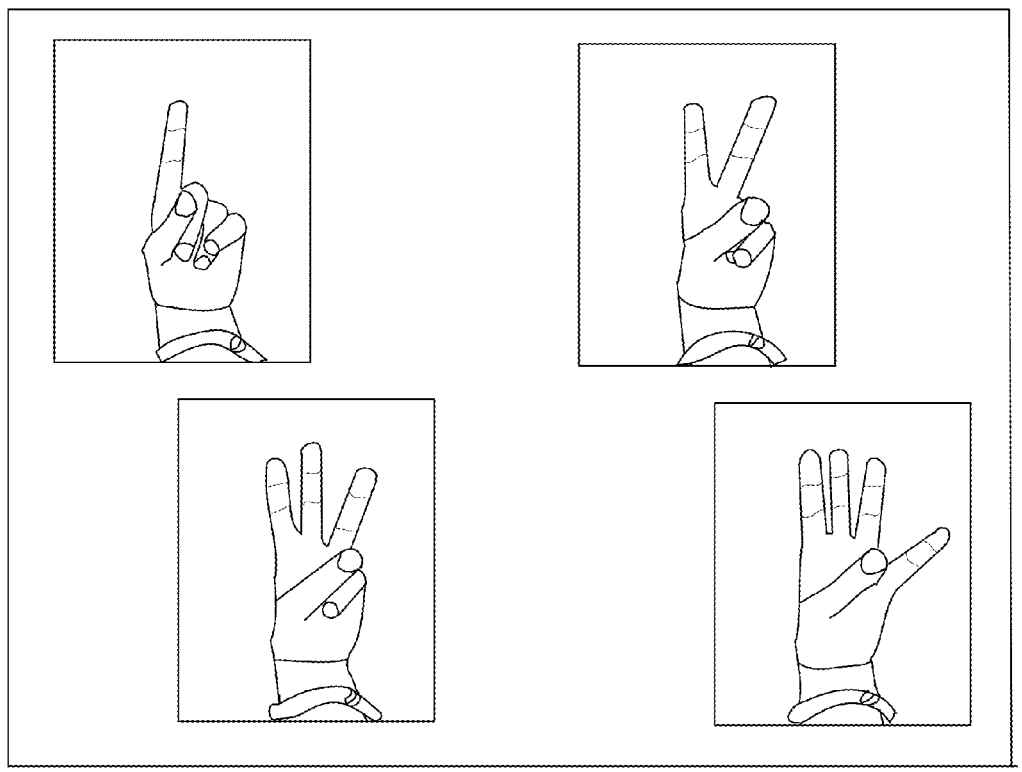
FIG. 10 is an exemplary EyeVoice screen that shows pictures of 4 different hands to test if a patient correctly answers a nurse's questions, in accordance with various embodiments.

The traditional administration of CAM-ICU's Feature 4B: "Disorganized Thinking—Command" requires the user to hold up a specified number of fingers. EyeVoice enables those patients to respond with gaze-based selections, rather than hold up their hand and extend their fingers. FIG. 10, for example, is a screen 1000 that shows pictures of 4 different hands, each holding up 1, 2, 3, and 4 fingers respectively. The nurse may hold up 2 fingers and ask the patient to "pick the hand with one more finger than 1 am showing." The patient answers correctly in this case by looking at the cell (or picture) displaying a hand with three fingers extended.

In various embodiments, the EyeVoice system would automatically record the patient responses to all the questions and automatically evaluate the patient's level of delirium based on the correctness of the answers. The EyeVoice's evaluation criteria would be based on the hospital's proscribed evaluation criteria.

Gaze-Based Patient Communication Screens

Figure 11:
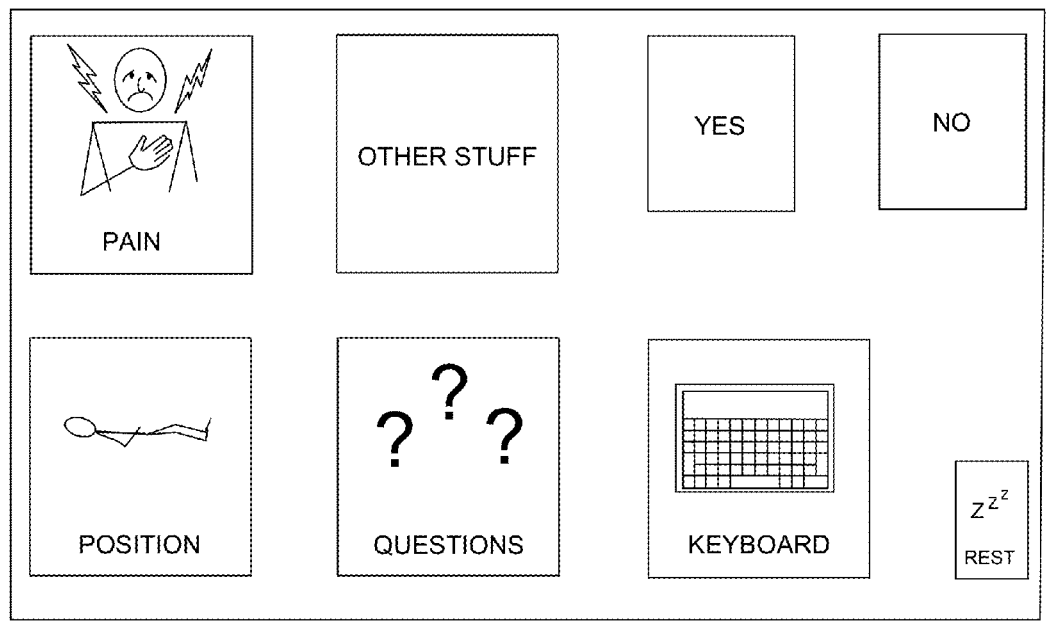
FIGS. 11 and 12 are exemplary patient communication screens, in accordance with various embodiments.
Figure 12:
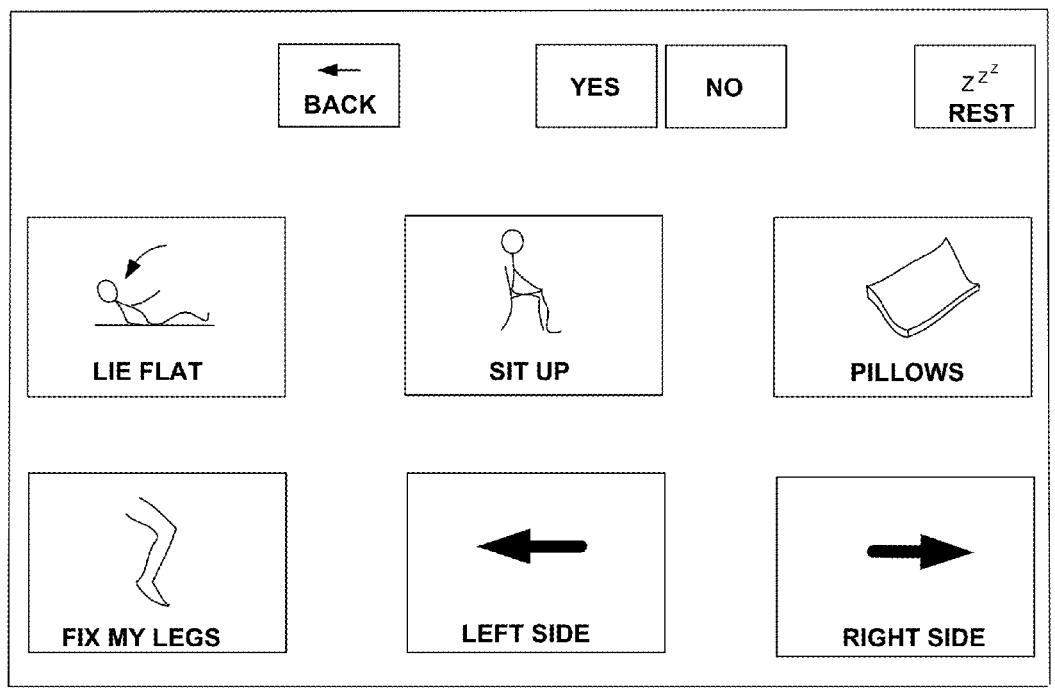

Examples of the patient communication screens are shown in FIGS. 11 and 12. Patients look at images or words to communicate their needs, and nurses confirm that their selection is intentional and correct. A Primary Display 1100, illustrated in FIG. 11, might contain selections for "Yes," "No," "Pain," and "Position." The "Questions" and "Keyboard" cells allow the patient to navigate to other communications screens that allow him to answer questions from the nurse, select issues he would like to address, or to type and speak text he wishes to compose.

If the patient selects "Position," a screen 1200 such as the one shown in FIG. 12 appears.

Gaze-Based Pain Evaluation

An important element of patient communications in a hospital involves asking the patient about the degree, location, and type of his pain. Patient pain-level scales are often designated using a numerical scale, with, for example, 1 being pain-free and 10 indicating excruciating pain. Other pain scales are expressed using colors, facial expressions or descriptive words. With color scales, for example, purple may signify no pain and red may indicate excruciating pain, with blue, green, gold and orange representing "bearable", "mildly painful", "painful," and "very painful."

Figure 13:
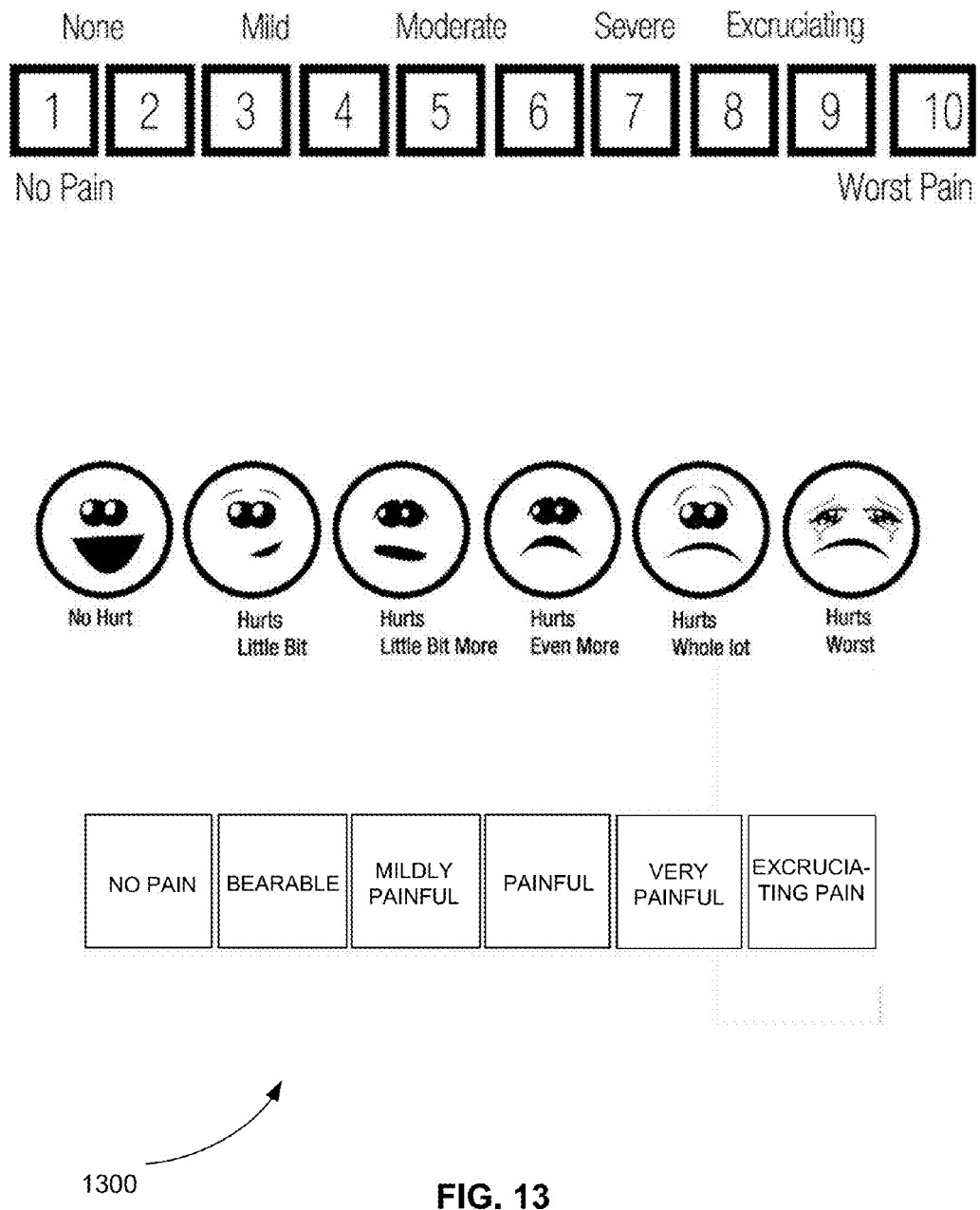
FIGS. 13, 14, and 15 illustrate exemplary EyeVoice screens that implement pain scale tests regarding the level, location, and type of pain, respectively, in accordance with various embodiments.
Figure 14:
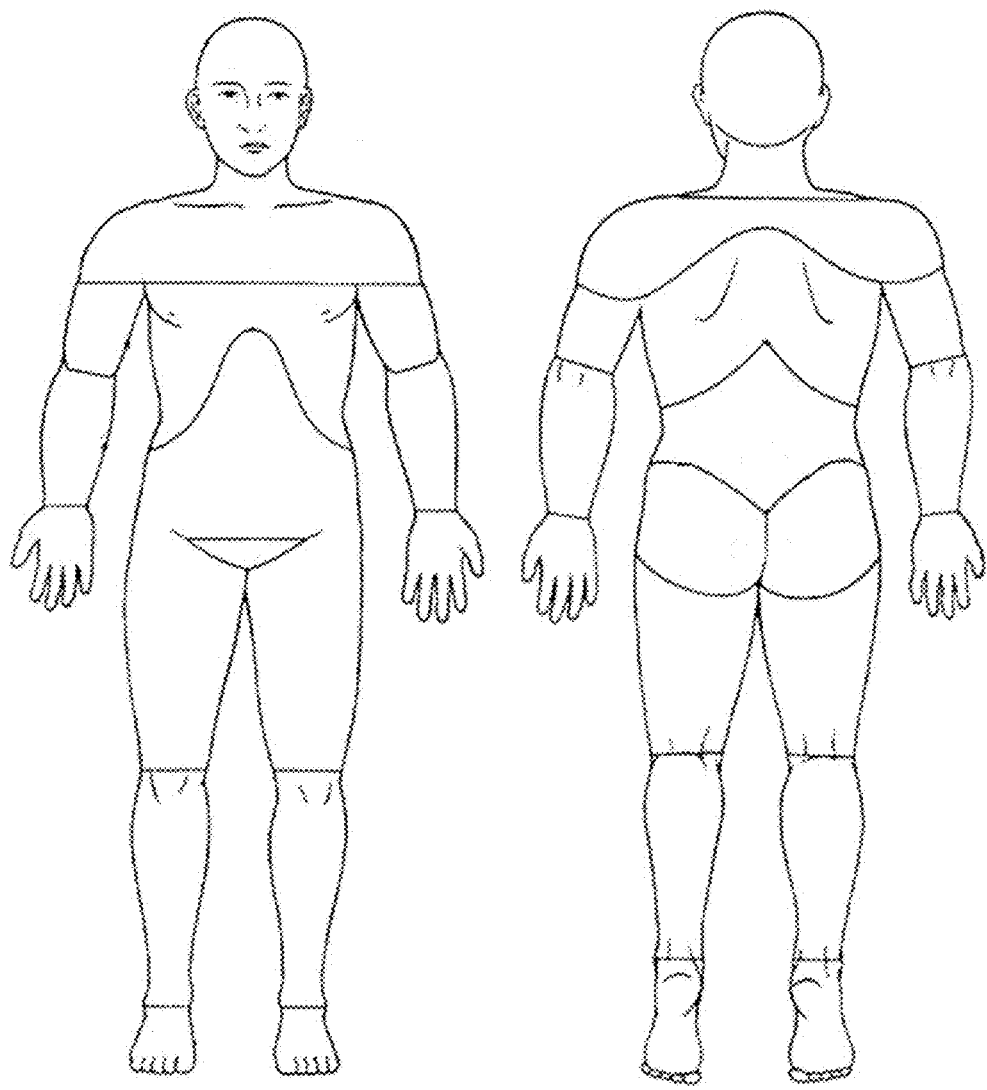
Figure 15:
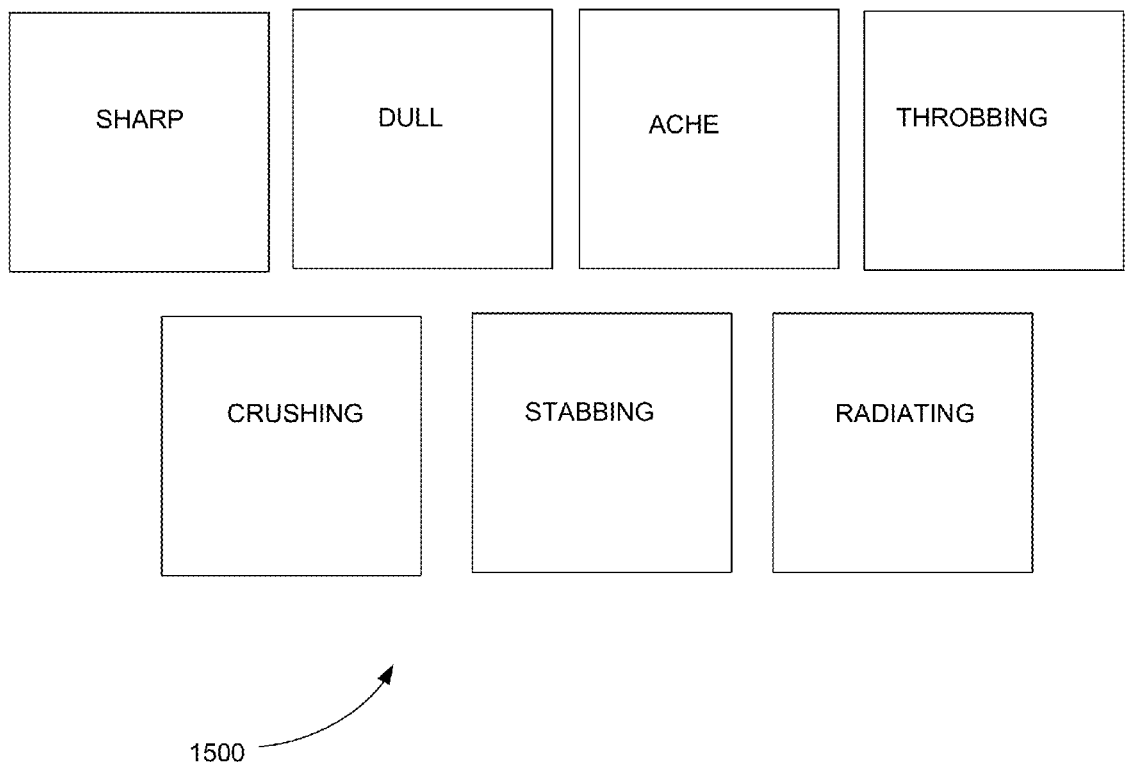

As illustrated in FIG. 13, EyeVoice implementations of pain scale tests typically present displays 1300 containing alternative images representing the different pain-levels, and the patient specifies his pain level by looking at the image representing his pain level. Similarly, as illustrated in FIG. 14, EyeVoice allow patients to specify the location of their pain by looking at alternative body-part images shown in display 1400. The patient may indicate pain type using screens 1500 that display alternative types, as illustrated in FIG. 15.

Sample Primary & Secondary Communication Screens

If the Primary Display offers a choice the patient wants, the patient looks at the topic's cell to select it. The patient is instructed to look at the "no" cell if the Primary Display does not provide the topic he wants. If the patient chooses a topic cell, EyeVoice verbalizes that selection and proceeds to the appropriate secondary screen for more detailed communication. The nurse may verify the patient's choice by asking him to look at her if his selection was intentional, and to look away if not. If he is able, the patient may select a keyboard from the Primary Display and type a unique message.

System for Communicating with Lock-In Patients

Referring again to FIG. 3, in various embodiments, system 300 can be used to communicate with locked-in patients. Visual display 330 can be used to display information to a patient 310 in a healthcare setting. Eyetracker 320 monitors a gazepoint trace of the patient's eyes within visual display 330. Processor 360 correlates the gazepoint trace of the patient's eyes with elements of the visual display. Processor 360 infers the patient's awareness of a situation by verifying that the patient has looked at one or more designated elements of the visual display.

In various embodiments, visual display 330 is for the patient, and a second visual display 350 is included for a caregiver. One skilled in the art will appreciate that processor 360 can be part of visual display 330, eyetracker 320, and second display 350.

In various embodiments, a monitor of visual display 330 for the patient and a second monitor of second visual display 350 for the caregiver are mounted back to back in an integrated unit.

System for Administering a Test to a Person Using a Gaze-Based System

Referring again to FIG. 3, system 300 can be used to administer a test to a person. Visual display 330 is used for displaying alternative answers to a plurality of questions. Eyetracker 320 monitors the person's gazepoint within the visual display. Processor 360 allows the person to select one of the displayed alternative answers by looking at the selected answer.

In various embodiments, the test is a hearing assessment test, and the plurality of questions include hearing-oriented questions.

In various embodiments, the test is an orientation and/or awareness test, and the plurality of questions include orientation- and/or awareness-oriented questions.

In various embodiments, the test is a delirium test, and the plurality of questions include delirium questions.

In various embodiments, processor 360 records the person's delirium answers and assesses the person's level of delirium based on a correctness of the person's delirium answers.

In various embodiments, the test is a pain-level assessment test, the alternative answers to the plurality of questions include two or more options corresponding to alternative levels of pain, and processor 360 allows the person to select allows the person to designate a pain level by looking at a corresponding pain-level option on the visual display.

In various embodiments, the test allows a person to designate a location of pain, the alternative answers to the plurality of questions include two or more options corresponding to alternative pain locations, and processor 360 allows the person to select allows the person to designate a pain location by looking at a corresponding pain-location option on the visual display.

In various embodiments, the test allows a person to designate a type of pain, the alternative answers to the plurality of questions include two or more options corresponding to alternative pain types, and processor 360 allows the person to select allows the person to designate a pain type by looking at a corresponding pain-type option on the visual display.

Method for Administering a Test to a Person Using a Gaze-Based System

Figure 16:
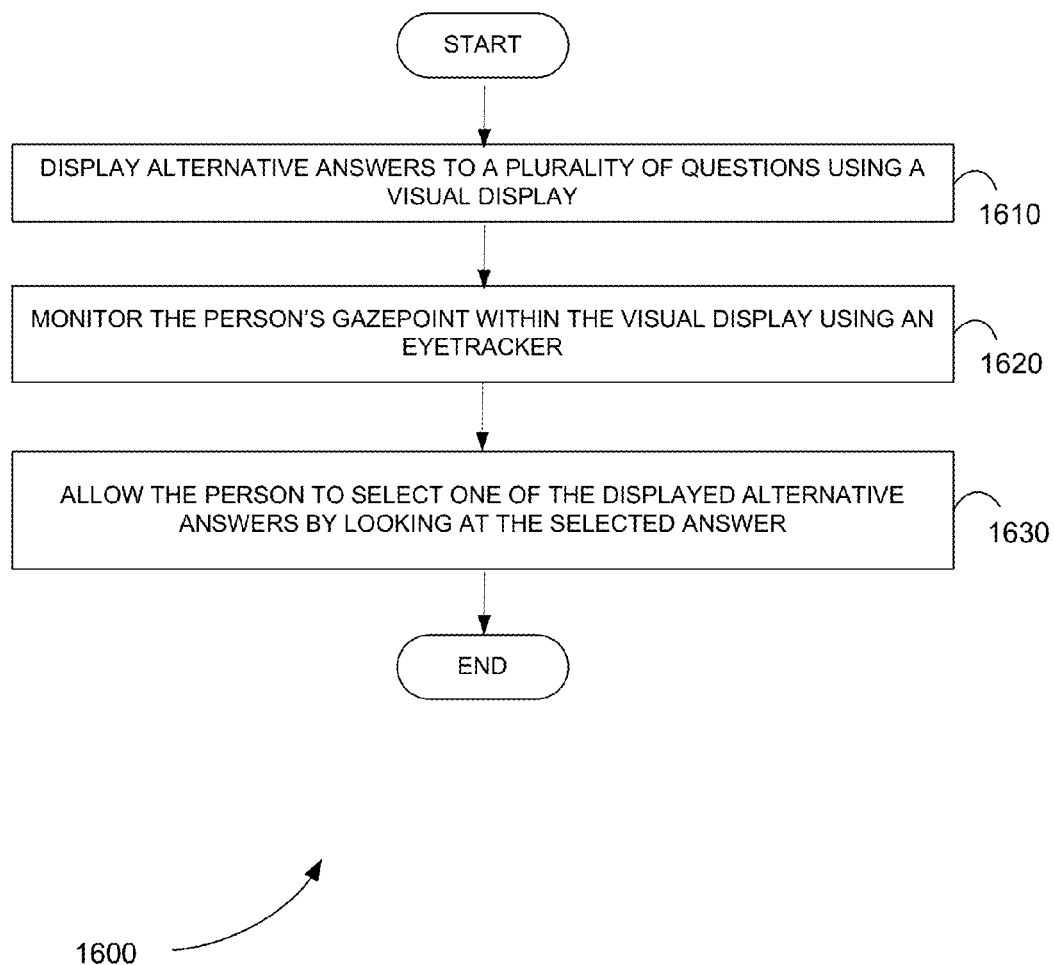
FIG. 16 is a flowchart showing a method for administering a test to a person using a gaze-based system.

FIG. 16 is a flowchart showing a method 1600 for administering a test to a person using a gaze-based system.

In step 1610 of method 1600, alternative answers to a plurality of questions are displayed to a person using a visual display.

In step 1620, the person's gazepoint within the visual display is monitored using an eyetracker.

In step 1630, the person is allowed to select one of the displayed alternative answers by looking at the selected answer.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for communicating with locked-in patients, including:
    a patient's visual display for displaying information to a patient in a healthcare setting;
    a caregiver's visual display for a caregiver;
    an eyetracker to monitor a gazepoint trace of the patient's eyes within the patient's visual display, wherein the eyetracker includes a camera mounted to the patient's visual display that images the patient's eye, an illumination source that illuminates the patient's eye, and one or more optical devices to determine the range from the camera to the patient's eye, and wherein the patient's visual display, the caregiver's visual display, and the camera are maneuverable to accommodate the position of the patient and the caregiver; and
    a processor that
        correlates the gazepoint trace of the patient's eyes with elements of the patient's visual display using the images of patient's eye and the range from the camera to the patient's eye,
        infers the patient's awareness of a situation by verifying that the patient has looked at one or more designated elements of the patient's visual display, and
        displays, on the caregiver's visual display, the images of the patient's eye and a gazepoint of the patient from the gazepoint trace, in addition to the same information displayed on the patient's visual display, providing the caregiver a) positive feedback that the eyetracking function is working, b) that the patient has his eyes opened or closed at any time, and c) an indication of what the patient is looking at as the patient looks around the patient's visual display and makes visual selections.

2. The system of claim 1 wherein a monitor of the patient's visual display and a second monitor of the caregiver's visual display are mounted back to back in an integrated unit.

3. The system of claim 1, wherein the eyetracker further records the images of the patient's eyes.

4. A gaze-based system for administering a test to a person, including:
- a person's visual display for displaying alternative answers to a plurality of questions;
- a caregiver's visual display for a person administering the test;
- an eyetracker that monitors the person's gazepoint trace within the person's visual display, wherein the eyetracker includes a camera mounted to the person's visual display that images the person's eye, an illumination source that illuminates the person's eye, and one or more optical devices to determine the range from the camera to the person's eye, and wherein the person's visual display, the caregiver's visual display, and the camera are maneuverable to accommodate the position of the person and the caregiver; and
- a processor that
  - allows the person to select one of the displayed alternative answers by looking at the selected answer by correlating the person's gazepoint with the alternative answers displayed on the person's visual display using the images of person's eye and the range from the camera to the person's eye, and
  - displays, on the caregiver's visual display, images of the person's eye and a gazepoint of the person from the gazepoint trace, in addition to the same alternative answers displayed on the person's visual display, providing the caregiver a) positive feedback that the eye-tracking function is working, b) that the person has his eyes opened or closed at any time, and c) an indication of what the person is looking at as the person looks around the person's visual display and makes visual selections.

5. The gaze-based system of claim 4, wherein the test is a hearing assessment test, and wherein the plurality of questions include hearing-oriented questions.

6. The gaze-based system of claim 4, wherein the test is an orientation and/or awareness test, and wherein the plurality of questions include orientation- and/or awareness-oriented questions.

7. The gaze-based system of claim 4, wherein the test is a delirium test, and wherein the plurality of questions include delirium questions.

8. The gaze-based system of claim 7, further comprising automatically recording the person's delirium answers and means for assessing the person's level of delirium based on a correctness of the person's delirium answers using the processor.

9. The gaze-based system of claim 4, wherein the test is a pain-level assessment test, and wherein the alternative answers to the plurality of questions include two or more options corresponding to alternative levels of pain, and wherein the means for allowing the person to select allows the person to designate a pain level by looking at a corresponding pain-level option on the person's visual display.

10. The gaze-based system of claim 4, wherein the test allows a person to designate a location of pain, and wherein the alternative answers to the plurality of questions include two or more options corresponding to alternative pain locations, and wherein the means for allowing the person to select allows the person to designate a pain location by looking at a corresponding pain-location option on the person's visual display.

11. The gaze-based system of claim 4, wherein the test allows a person to designate a type of pain, and wherein the alternative answers to the plurality of questions include two or more options corresponding to alternative pain types, and wherein the means for allowing the person to select allows the person to designate a pain type by looking at a corresponding pain-type option on the person's visual display.

12. A method for administering a test to a person using a gaze-based system, including:
- displaying alternative answers to a plurality of questions using a person's visual display;
- monitoring the person's gazepoint trace within the person's visual display using an eyetracker, wherein the eyetracker includes a camera mounted to the person's visual display that images the person's eye, an illumination source that illuminates the person's eye, and one or more optical devices to determine the range from the camera to the person's eye, and wherein the person's visual display, a caregiver's visual display, and the camera are maneuverable to accommodate the position of the person and the caregiver;
- allowing the person to select one of the displayed alternative answers by looking at the selected answer by correlating the person's gazepoint with the alternative answers displayed on the person's visual display using a processor using the images of person's eye and the range from the camera to the person's eye; and
- displaying, on the caregiver's visual display, images of the person's eye and a gazepoint of the person from the gazepoint trace, in addition to the same alternative answers displayed on the person's visual display, providing the caregiver a) positive feedback that the eye-tracking function is working, b) that the person has his eyes opened or closed at any time, and c) an indication of what the person is looking at as the person looks around the person's visual display and makes visual selections.

13. The method of claim 12, wherein the test is a hearing assessment test, and wherein the plurality of questions include hearing-oriented questions.

14. The method of claim 12, wherein the test is an orientation and/or awareness test, and wherein the plurality of questions include orientation- and/or awareness-oriented questions.

15. The method of claim 12, wherein the test is a delirium test, and wherein the plurality of questions include delirium questions.

16. The method of claim 12, further comprising automatically recording the person's delirium answers and assessing the person's level of delirium based on a correctness of the person's delirium answers.

17. The method of claim 12, wherein the test is a pain-level assessment test, and wherein the alternative answers to the plurality of questions include two or more options corresponding to alternative levels of pain, and wherein the step of allowing the person to select comprises allowing the person to designate a pain level by looking at a corresponding pain-level option on the person's visual display.

18. The method of claim 12, wherein the test allows a person to designate a location of pain, and wherein the alternative answers to the plurality of questions include two or more options corresponding to alternative pain locations, and wherein the step of allowing the person to select comprises allowing the person to designate a pain location by looking at a corresponding pain-location option on the person's visual display.

19. The method of claim 12, wherein the test allows a person to designate a type of pain, and wherein the alternative answers to the plurality of questions include two or more options corresponding to alternative pain types, and wherein the step of allowing the person to select comprises allowing the person to designate a pain type by looking at a corresponding pain-type option on the person's visual display.

20. The method of claim 12, further comprising recording the images of the person's eye.

* * * * *